(12) United States Patent
Elmaleh et al.

(10) Patent No.: US 9,452,041 B2
(45) Date of Patent: Sep. 27, 2016

(54) DELIVERY SYSTEM FOR INTRAVASCULAR DEVICE WITH NETTING

(76) Inventors: David R. Elmaleh, Newton, MA (US); Boyan C. Goumnerov, Wayland, MA (US)

(*) Notice: Subject to any disclaimer, the term of this patent is extended or adjusted under 35 U.S.C. 154(b) by 735 days.

(21) Appl. No.: 12/633,402

(22) Filed: Dec. 8, 2009

(65) Prior Publication Data
US 2010/0204773 A1 Aug. 12, 2010

Related U.S. Application Data

(63) Continuation-in-part of application No. 11/369,128, filed on Mar. 6, 2006, now Pat. No. 8,597,341, and a continuation-in-part of application No. 11/788,008, filed on Apr. 18, 2007, now Pat. No. 8,801,777.

(60) Provisional application No. 61/120,717, filed on Dec. 8, 2008.

(51) Int. Cl.
| | | |
|---|---|---|
| A61F 2/06 | (2013.01) | |
| A61F 2/07 | (2013.01) | |
| A61F 2/958 | (2013.01) | |
| A61F 2/852 | (2013.01) | |
| A61F 2/90 | (2013.01) | |

(52) U.S. Cl.
CPC ............... *A61F 2/07* (2013.01); *A61F 2/852* (2013.01); *A61F 2/958* (2013.01); *A61F 2/90* (2013.01); *A61F 2002/075* (2013.01); *A61F 2002/9583* (2013.01); *A61F 2250/0063* (2013.01)

(58) Field of Classification Search
CPC .... A61F 2/07; A61F 2/958; A61F 2002/075; A61F 2002/9583; A61F 2250/0063; A61F 2/90; A61F 2/852
USPC ............ 606/1.11, 108; 623/1.13, 1.16, 1.11, 623/1.36, 1.44, 1.15, 1.23, 136, 910; 29/282; 604/96.01
See application file for complete search history.

(56) References Cited

U.S. PATENT DOCUMENTS

| | | | | |
|---|---|---|---|---|
| 5,201,757 | A * | 4/1993 | Heyn et al. | 606/198 |
| 5,409,495 | A * | 4/1995 | Osborn | 623/1.11 |
| 5,630,830 | A * | 5/1997 | Verbeek | 606/198 |
| 5,639,274 | A * | 6/1997 | Fischell et al. | 604/96.01 |
| 5,759,186 | A * | 6/1998 | Bachmann et al. | 606/108 |
| 6,027,510 | A * | 2/2000 | Alt | 606/108 |
| 6,143,022 | A * | 11/2000 | Shull et al. | 623/1.13 |
| 6,306,162 | B1 * | 10/2001 | Patel | 623/1.11 |
| 6,589,274 | B2 * | 7/2003 | Stiger et al. | 623/1.11 |
| 6,986,786 | B1 * | 1/2006 | Smith | 623/1.36 |
| 7,235,093 | B2 * | 6/2007 | Gregorich | 623/1.11 |
| 2001/0049554 | A1 * | 12/2001 | Ruiz et al. | 623/1.44 |
| 2002/0010489 | A1 * | 1/2002 | Grayzel et al. | 606/194 |

(Continued)

*Primary Examiner* — Richard Louis
(74) *Attorney, Agent, or Firm* — Dinsmore & Shohl LLP (57) ABSTRACT

In a cardiac double stent having an outer netting over an inner scaffolding, a limiting ridge for defining advancement of the outer netting over the inner scaffolding, and locking clips integrated in the outer netting for engaging the scaffolding at the insertion limit, assures definite placement and avoids shifting or movement from retracting of the delivery device. The delivery device further includes restricting ridges limiting advancement of the inner netting to overlie the inner scaffolding a substantially equal portion on the proximate and distal ends of a guide wire such that balloon catheter expands first at the overlying portion outside the inner scaffolding to sealably contact the lumen wall on each side of the scaffolding to prevent contamination.

14 Claims, 6 Drawing Sheets

(56) References Cited

U.S. PATENT DOCUMENTS

| | | | |
|---|---|---|---|
| 2003/0171799 A1* | 9/2003 | Lee et al. | 623/1.11 |
| 2004/0138731 A1* | 7/2004 | Johnson | 623/1.11 |
| 2005/0192662 A1* | 9/2005 | Ward | 623/1.16 |
| 2005/0267561 A1* | 12/2005 | Jones et al. | 623/1.11 |
| 2005/0288768 A1* | 12/2005 | Sowinski et al. | 623/1.13 |
| 2006/0129223 A1* | 6/2006 | Jabbour et al. | 623/1.11 |
| 2006/0178723 A1* | 8/2006 | Lentz et al. | 623/1.13 |
| 2009/0030510 A1* | 1/2009 | Ho | 623/2.11 |
| 2010/0057096 A1* | 3/2010 | Wolf | 606/108 |

* cited by examiner

DELIVERY SYSTEM FOR INTRAVASCULAR DEVICE WITH NETTING

RELATED APPLICATIONS

This application claims the benefit under 35 U.S.C. 119(e) of U.S. Provisional 61/120,717, filed Dec. 8, 2008, entitled "Delivery System for Intravascular Device with Netting", and the benefit under 35 U.S.C. 120 as a continuation-in-part of U.S. patent application Ser. No. 11/369,128, filed Mar. 6, 2006, entitled "Intravascular device with Netting System," and Ser. No. 11/788,008, filed Apr. 18, 2007, entitled "Intravascular device with Netting System", all incorporated herein by reference in entirety.

BACKGROUND

Many medical intravascular devices are currently being used either temporarily or permanently inside the human body to address conditions associated with high blood pressure, diabetes, and stroke. One example of an intravascular device is a stent for use in, for instance, coronary angioplasty. Stents are small mechanical devices that can be implanted within a vascular structure, such as a blood vessel or an artery, and can be mechanically expanded to maintain an open lumen at a constricted location to permit a substantially clear flow path therethrough. A stent can also act to support a vessel wall in areas vulnerable to collapse.

The mechanical reopening of a constricted vessel can sometimes lead to injuries of the tissues at the site of constriction or closure. Such injuries can often stimulate thrombus formation at such a site, as well as release of tissue debris that may subsequently act to block fluid flow within the vessel. Moreover, if permitted to proliferate, pronounced neointimal hyperplasia or restenosis can result. Thrombus production remains one of the most common post-stenting clinical problem, and requires effective intervention or counter-measures to prevent and/or control its reoccurrence.

Currently, methods for preventing or controlling thrombus are specifically aimed at influencing factors believed to be involved in the body's response to external or internal tissue stimulants, such as angioplasty, stenting procedures, and/or viruses. Common countermeasures which have been used to prevent or control restenosis generally fall into the one of several categories, including (1) mechanical atheroablative techniques, such as debulking, vascular filters, and emboli-trapping devices, (2) ultrasound-initiated atheroablative techniques, (3) light-assisted procedures, predominantly excimer laser angioplasty, (4) pharmacological agents and gene therapy, (5) ultraviolet photophoresis, believed to be an immune modulator, (6) radiation therapy, such as external and endovascular brachytherapy, and (7) re-stenting.

In addition, modifications to stent designs and materials have been proposed to prevent and/or control restenosis. In one approach, non-metallic, biodegradable stent materials, such as high molecular weight Poly-1-lactic acid (PLLA) is used.

Numerous inorganic coatings and surface treatments have also been developed to improve chemical inertness and biocompatibility of metallic stents. Some coatings, such as gold, however, yield a higher rate of in-stent restenosis than uncoated stents. Others, including silicon carbide and turbostatic carbon, show promise but additional studies must be done.

Organic coatings, including both synthetic and natural coatings, have also been widely studied. Among the synthetic coatings studied are Dacron, polyester, polyurethane, polytetrafluoroethylene (PTFE), polyethylacrylate/polymethylmethacrylate, polyvinyl chloride, silicone, collagen, and iridium oxide.

Results of studies, such as those with PTFE-coated stents, are disappointing or mixed at best, as there are high occurrences of late thrombo-occlusive events. With only a very few exceptions, the general consensus is that any favorable outcome was not associated with treatment of conventional in-stent restenosis using PTFE-coated stents.

Intracoronary intervention have also been employed to reduce neointima formation by reducing smooth muscle cell proliferation after balloon angioplasty. However, such intervention is often complicated by subacute and late thrombosis. Coronary thrombo-aspdrugiration and coronary pulsed-spray procedures, followed by immediate endovascular therapy, have also been particularly helpful in removing thrombotic material associated with plaque.

In addition, pharmacotherapeutic agents have been used for the treatment of some of the major post-angioplasty complications, including immunosuppresants, anticoagulants and anti-inflammatory compounds, chemotherapy agents, antibiotics, antiallergenic drugs, cell cycle inhibitors, gene therapy compounds, and ceramide therapy compounds. Pharmacotherapeutic agents can be delivered either systemically or locally. Systemic treatment has shown limited success in reducing restenosis following stent implantation, a result believed to be due to inadequate concentration of the pharmacotherapeutic agents at the site of injury. Increased dose administration, however, is constrained by possible systemic toxicity. It has been observed that local delivery of higher doses via drug eluting stents can significantly reduce adverse systemic effects. However, the local delivery of drugs via stents may be limited by the amount of surface area for drug elution.

Gene therapy have also been employed in the treatment of thrombus production. The procedure is directed towards smooth muscle cells and involves gene transfer via DNA, with or without integration of chromosomes, into selected cells. In transduction without integration, the gene is delivered to both cytoplasm and nucleus and is therefore non-selective. Gene transfer for integration employs retrovirus to affect growth stimulators.

Antibiotics, likewise, has been used in the treatment of coronary artery disease. It is known that antibiotics are effective in controlling inflammation caused by a variety of infectious agents found in fatty plaques blocking the arteries. Results of clinical investigation, such as with azithromycin, suggest a modest antibiotic benefits for heart patients.

Similarly, a phospholipid exhibiting immunosuppressive properties, has been shown to block T-cell activation and proliferation, inhibit Taxol-induced cell cycle apoptosis, and activate protein kinase signal translation in malignant myogenic cells. Rapamycin and its analogs exhibit anti-tumor activities at relatively low dose levels, while inducing only mild side effects, an extremely important aspect of patient care.

SUMMARY

The present invention provides, in one embodiment, an intravascular device, such as a stent, for keeping open a previously constricted intravascular site within a vessel and for minimizing tissue debris from such a site from closing off the vessel. The device may also be used for local delivery of at least one pharmacotherapeutic agent to the intravascular site for the treatment or prevention of restenosis.

The intravascular device, in accordance with an embodiment of the invention, includes an expandable substantially tubular body for placement against a vessel wall. The body of the device, in a particular configuration, may be defined by a framework having a plurality of openings. The device also includes a flexible netting system having a structural design for extending across each of the openings. Such a double stent design allows the netting system to expand along with each opening in the framework to minimize occurrence of thrombus formation and tissues debris from closing the lumen of the vessel. The netting system can include a plurality of pores to permit communication between fluid flow within the vessel and the vessel wall, and at least one pharmacotherapeutic agent for the treatment or prevention of certain conditions. In one embodiment, the netting system includes a plurality of extensible panels, each designed to be securely situated within an opening of the matrix. Alternatively, the netting system includes a mesh disposed on a substantially flexible matrix, such that the mesh can be placed circumferentially about the framework of the body. If desired, the flexible matrix can be provided with sufficient strength to permit the netting system to keep the lumen of the vessel temporarily open until the framework can be expanded. The device of the present invention, in an embodiment, can further include a second expandable substantially tubular framework concentrically positioned within the first framework of the tubular body.

The present configuration also provides a method for the placement of such an intravascular device within a vessel. The method includes initially providing a device having an expandable substantially tubular body defined by a framework having a plurality of openings, and a plurality of netting panels situated within each of the openings. Next, the device may be advanced along a lumen of the vessel to a site of interest. Thereafter, the framework may be expanded at the site of interest to allow the lumen of the vessel to remain open. The device may subsequently act to elute at least one pharmacotherapeutic agent for treatment of a condition from the netting panels. The netting panels may also act to retain tissue debris between the netting panels and a vessel wall.

The present invention further provides another method for placement of an intravascular device within a vessel. The method includes providing a device having an expandable substantially tubular body defined by an inner framework or scaffolding having a plurality of openings, and an outer mesh or netting disposed on a substantially flexible matrix loosely positioned circumferentially about the framework. Next the device may be advanced along a lumen of the vessel to a site of interest. Thereafter, the framework may be expanded at the site of interest, and the mesh on the flexible matrix be allowed to be secured between the framework and a vessel wall. In one embodiment, prior to expanding the framework, the flexible matrix on which the mesh is disposed may be expanded. The device may subsequently act to elute, from the mesh, at least one pharmacotherapeutic agent for treatment of a condition. The mesh may also act to retain tissue debris between the netting panels and a vessel wall.

Conventional approaches suffer form the shortcoming that delivery of the outer netting over the inner scaffolding is difficult to position such that the balloon catheter is positioned substantially centered and overlying the inner scaffolding. Configurations herein are based, in part, on the observation that imprecise centering of the outer netting over the inner scaffolding may result in unequal balloon catheter expansion that may compromise stent placement.

Accordingly, configurations herein substantially overcome such shortcomings by providing a limiting ridge for defining advancement of the outer netting over the inner scaffolding, and locking clips integrated in the outer netting for engaging the scaffolding at the insertion limit to avoid shifting or movement from retracting of the delivery device. The delivery device further includes restricting ridges limiting advancement of the inner netting to overlie the inner scaffolding by a substantially equal portion on the proximate and distal ends such that balloon catheter expands first at the overlying portion outside the inner scaffolding to sealably contact the lumen wall on each side of the scaffolding to prevent contamination. Alternate configurations of the invention include various arrangements for delivering a double stent apparatus, such as that disclosed in the copending U.S. patent applications cited above for delivering a stent into a lumen or vessel as disclosed and claimed herein for performing the techniques explained herein as embodiments of the invention.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Configurations described below depict various configurations of the double stent and delivery and installation thereof, as in placement in a lumen of a blood vessel. In a particular configuration, the delivery system includes a balloon catheter with limiting (restricting ridges) at proximal and distal ends of balloon; a scaffolding stent placed circumferentially around the balloon between ridges; and self expanding netting with latching devices (hooks) retained in a delivery sleeve which is placed circumferentially over the body of the main balloon catheter and can be advanced and retracted along the axis of the catheter. The internal diameter of the netting is slightly larger than the outer diameter of ridges which allows the advancement of the netting on top of the scaffolding stent.

In operation, following the delivery of the scaffolding stent to the target area in the vessel, the sheet containing the self expanding netting is advanced forward until the proximal ridge on the catheter limits further advancement of the sheet when the inner edge of the delivery sheet at the proximal end of the netting. Following advancement of the netting over the scaffolding stent the locking (attaching) hooks (mechanism) engages the scaffolding stent. Next, the delivery sleeve for the netting is retracted while the netting remains in position due to its attachment to the scaffolding stent and expands as it is released from the sleeve.

In contrast to conventional mechanisms, the netting is delivered to the target area in sequence (scaffolding first, netting on top second which eventually is followed by expansion). This allows for greater flexibility of the device compared to a conventional preassembled double metal structure which will be much more rigid and difficult to deliver to the target area. Following the retraction of the netting delivery sleeve and expansion of the netting, the balloon is inflated and the scaffolding stent is expanded to the desired diameter thus locking the netting between the vessel wall and stent. The balloon is deflated and the entire delivery system is retracted.

Figure 1:
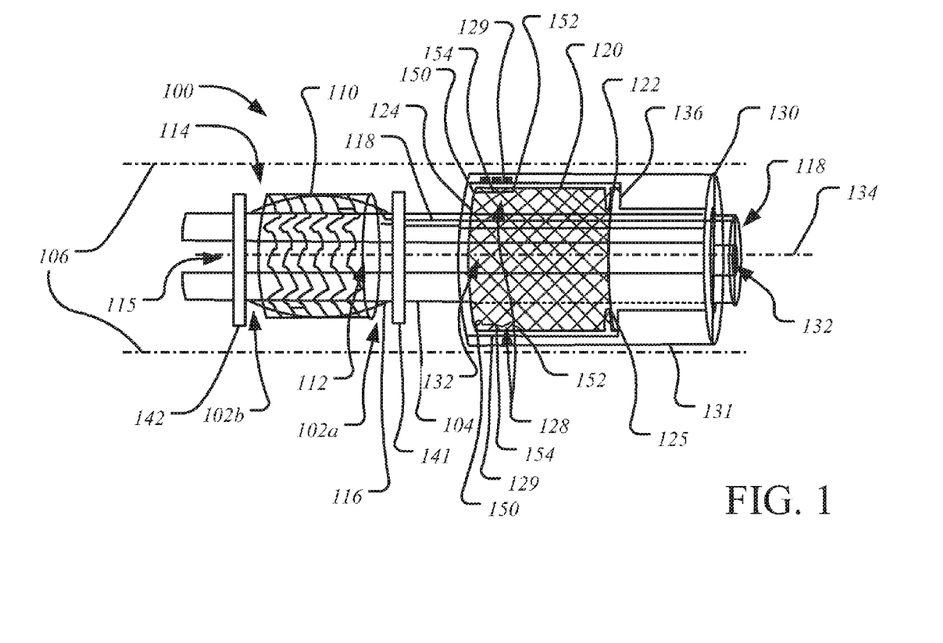
FIG. 1 shows a side view of a particular configuration of the double stent and delivery device.

FIG. 1 shows a side view of a particular configuration of the double stent and delivery device. Referring to FIG. 1, the double stent (stent) 100 includes an inner scaffolding 110 and an outer netting 120 adapted for slideable disposition via a catheter 104. A delivery device 130 advances the outer netting 120 over the inner scaffolding 110 to install the double stent 100, discussed further below. The stent 100 includes restricting ridges 141 and 142, at proximate (141) and distal (121) ends from the delivery device 130, which align with proximate 125 and distal 124 opening in the outer netting 120 following advancement. A guide wire channel 132 retains a guide wire 134 in slideable communication with the delivery device 130 for advancing the outer netting 120 over the inner scaffolding 110. A limiting ridge 136 engages a proximate end 122 of the inner netting 120 for advancing the netting 120 over the scaffolding 110. A proximate restricting ridge 141 limits advancement by engaging the limiting ridge 136 at a point which the outer netting 120 is substantially centered over the inner scaffolding 110 such that overlying regions 102a and 102b (102 generally) are defined between a proximate opening 112 and a distal opening 114 and the corresponding proximate and distal restricting ridges 141, 142, respectively. After full advancement, withdrawal of the delivery device 130 activates locking clips 128 such that anterior hooks 150 engage the inner scaffolding to secure the outer netting through integrated posterior hooks 152 attached via an arm 154.

A balloon 116 occupies a cylindrical cavity 115 in the inner scaffolding 110 and couples to an inflation channel 118 adjacent the guide wire 134. Following delivery of the outer netting 120 over the inner scaffolding 110, inflation of the balloon 116 causes radial expansion of the inner scaffolding 110. As the balloon 116 commences expansion, the overlying regions 102a and 102b define expansion regions unrestrained by the inner scaffolding 110 such that the balloon 116 forms an expansion bubble 119, discussed further below in FIG. 8, for sealably engaging the delivered outer netting 120 against a lumen wall 106 defined by the vessel into which the stent 100 is inserted, thus preventing contamination in the region between the inner scaffolding 110 and the lumen wall 106.

In a second configuration, the delivery system includes a balloon catheter with retainers, a scaffolding stent placed on top of the balloon; and netting placed circumferentially around scaffolding stent which is held in place by the retainers which overly the proximal and distal end of the netting. The retainers are flexible so as to be withdrawn through the scaffolding following expansion of the stent 100.

Figure 2:
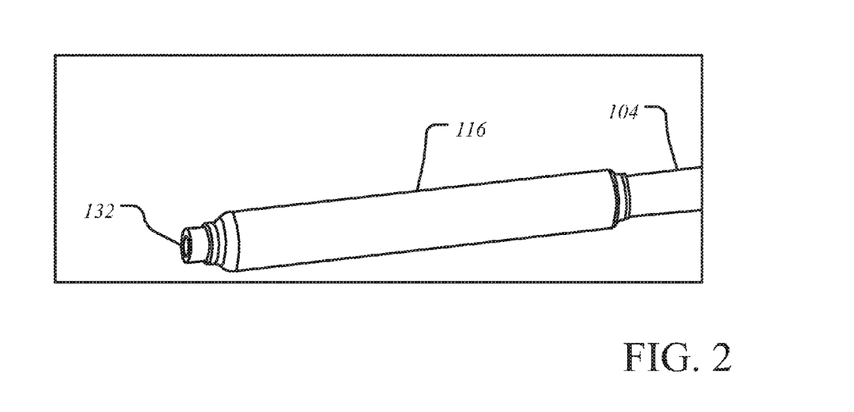
FIG. 2 shows a second configuration including an expandable balloon catheter for insertion in the double stent.

FIG. 2 shows the second configuration including an expandable balloon catheter 104 for insertion in the double stent of FIG. 1. Referring to FIGS. 1 and 2, the balloon 116 expands from compressed air or any suitable fluid delivered via the inflation channel 118. The balloon 116 expands radially to install the stent 100 including the inner scaffolding 110 and outer netting 120, now discussed in further detail.

Figure 3:
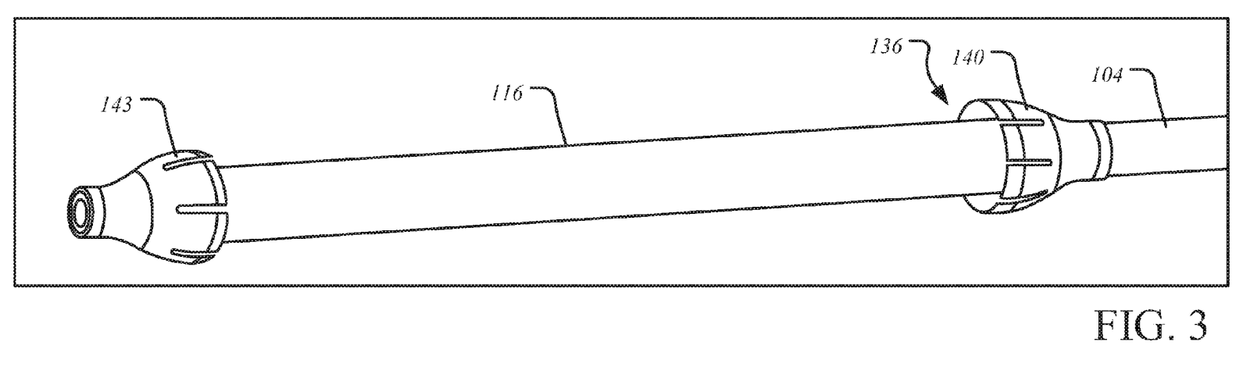
FIG. 3 shows retainers of the delivery device around the balloon catheter of FIG. 2.

FIG. 3 shows retainers 140, 143 of the delivery device around the balloon catheter of FIG. 2. Referring to FIGS. 1 and 3, a pair of retainers include a proximate retainer 140 and a distal retainer 143, the distal retainer 143 furthest advanced along the catheter 104. In a particular arrangement, the proximate retainer 140 includes the limiting ridge 136 for advancing the inner netting 120, effectively performing the operations of the delivery device 130. Alternatively, a separate delivery device 130 may be extended and retracted, as discussed below.

In operation, the balloon catheter 116 and stent 100 assembly is advanced until the stent 100 reaches the target area. The balloon is inflated which causes its expansion initially at the proximal and distal ends which pushes the netting ends out from underneath the flexible (elastic) retainers and against the vessel wall. As the pressure in the balloon 116 builds up the scaffolding stent 110 and outer netting 120 above it are also pushed against the vessel wall 106. The balloon 116 is deflated and the catheter is retracted. The delivered stent assembly 100 includes the outer netting 120 over the inner scaffolding 110 stent assembly and the retainers 140, 143 which keep the assembly together until delivery.

Following delivery and expansion of the stent assembly 100 including the inner scaffolding 110 and outer netting 120, retraction includes retracting the distal retainer 143 and the proximate retainer 140 through the inner scaffolding 110 after expansion and deflation of the balloon 116 leaving the outer netting 120 around the inner scaffolding 110.

Figure 4:
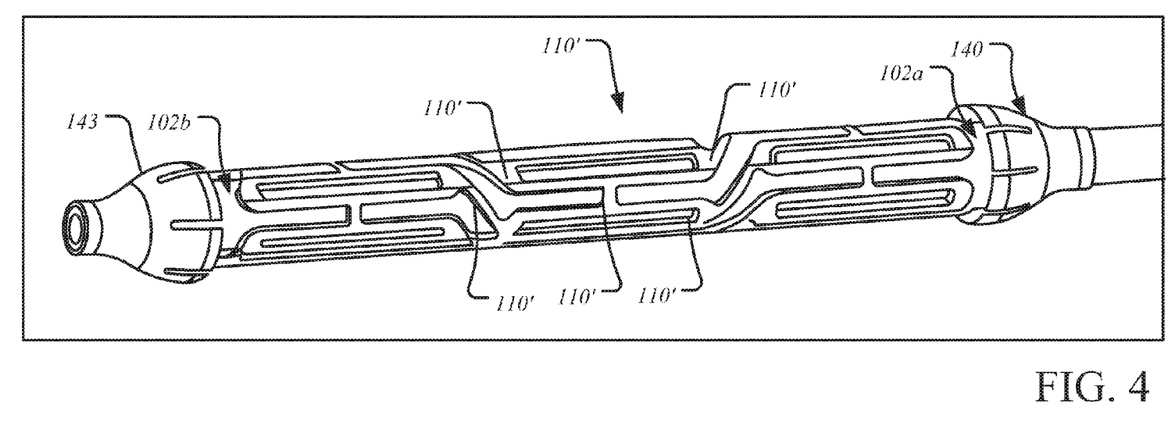
FIG. 4 shows the inner scaffolding around the balloon catheter of FIG. 3.
Figure 5:
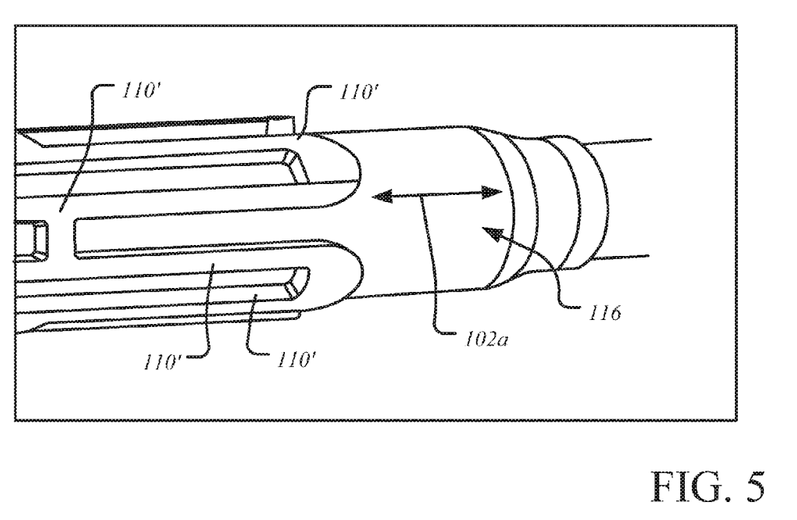
FIG. 5 shows an extension region of the balloon catheter of FIG. 4.

FIG. 4 shows the inner scaffolding 110 around the balloon catheter of FIG. 3. Referring to FIGS. 3, 4 and 5, the inner scaffolding 110 includes a plurality of flexible members 110' in an interconnected matrix for permitting radial expansion in response to balloon 116 inflation. An extension region 102a, 102b denotes an area where the balloon 116 extends beyond the ends 112, 114 of the inner scaffolding 110. The extension regions 102a and 102b are substantially equal from centering of the inner scaffolding 110 over the balloon 116. FIG. 5 shows the extension region 102a of the balloon catheter of FIG. 4, which allows the balloon 116 to inflate unrestrained by the inner scaffolding 110, thus permitting sealable engagement with the lumen wall 106 and the outer netting 120.

Figure 6:
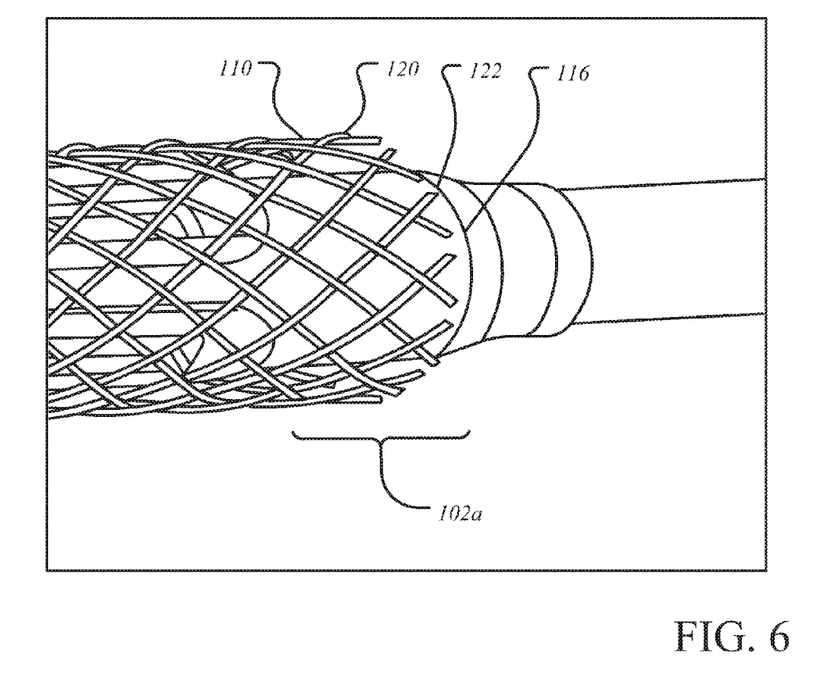
FIG. 6 shows the outer netting disposed around the inner scaffolding.

FIG. 6 shows the outer netting 120 disposed around the inner scaffolding 110. The inner scaffolding 110 is disposed centered between the ends 122, 124 of the outer netting 122 such that the extension region 102a is defined by the portion of the balloon 116 underlying the outer netting 120 and unconstrained from the inner scaffolding 110.

Figure 7:
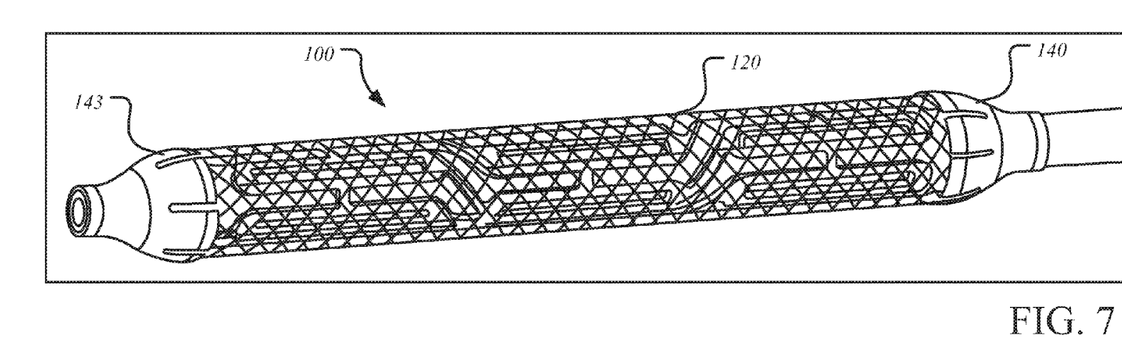
FIG. 7 shows the outer netting installed by the retainers.

FIG. 7 shows the outer netting 120 installed by the retainers 140, 143. The proximate retainer 140 may define the delivery device 130 by including the cylindrical cavity 131 for containing the outer netting and limiting ridge 136 for positioning the outer netting 120 substantially centered over the inner scaffolding 110 between the proximate and distal restricting ridges 141 and 142, respectively.

Figure 8:
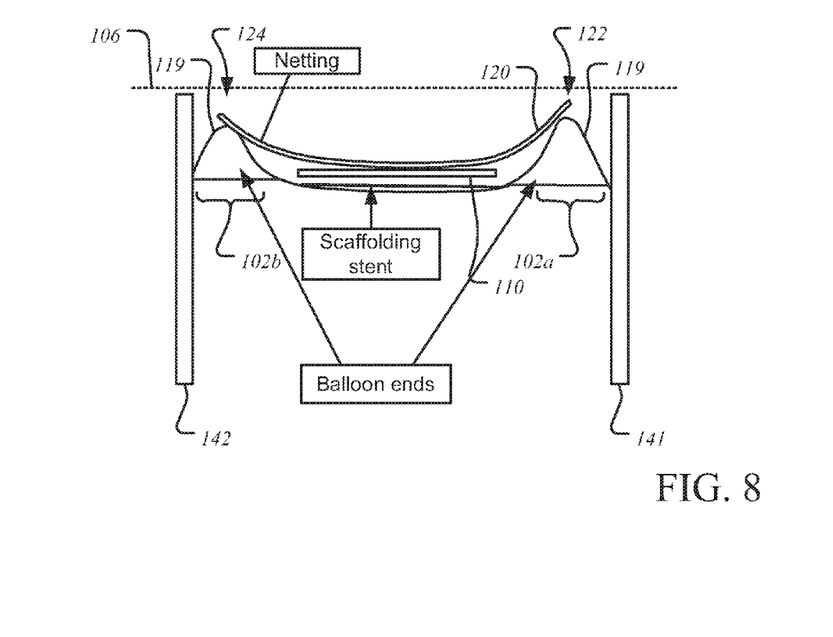
FIG. 8 shows an cross section of the axial plane of the balloon and extension region adjacent the inner scaffolding of FIG. 5.

FIG. 8 shows an cross section of the axial plane of the balloon 116 and extension region 102a adjacent the inner scaffolding 110 of FIG. 5. Referring to FIGS. 1, 5 and 8, the restricting ridges 141 and 142 define the location of the openings 122, 124 of the outer netting 120 following delivery. Such delivery disposes the outer netting 120 substantially centered over the inner scaffolding 110 such that the extension regions 102a, 102b are formed by the netting 120 portion overlying the scaffolding 110 and concentric with the balloon 116. Balloon 116 inflation results in expansion bubbles 119 forming along the ends 122, 124 and adjacent to the restricting ridges 141 and 142 unconstrained by the inner scaffolding 110. The expansion bubble 119 seals the lumen wall 106 against the balloon 116 and outer netting 120 to restrict debris before the remainder of the balloon 116 radially expands the inner scaffolding 110 against the netting 120 and lumen wall 106 to complete installation.

Therefore, the body of the catheter 104 facilitates the expansion bubble 119 in the extension region 102a and 102b from the ring-like restricting ridges 141 and 142 and the proximal and distal ends of the balloon 116 which have an external diameter equal to the external diameter of the inner scaffolding 110 as it is crimped on top of the balloon 116. The restricting ridges 141 and 142 prevent movement of the inner scaffolding 110 during introduction of the outer netting 120 such that friction between the resilient (springy) locking clips 128 does not dispose the scaffolding 110 forward and also to insure exact placement of the netting 120 above the scaffolding 110 by engaging the limiting ridge 136 of the delivery device 130.

Figure 9:
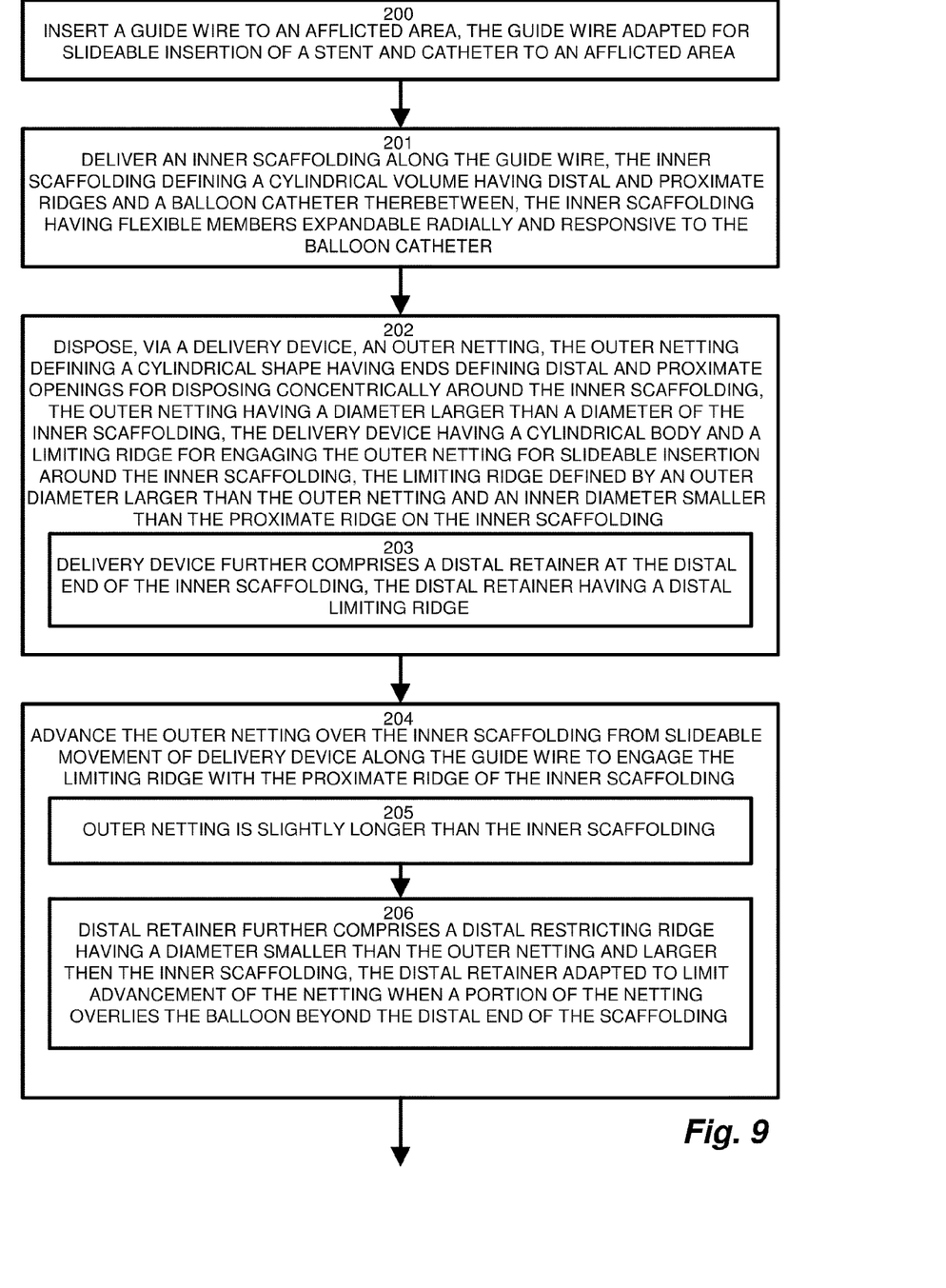
FIGS. 9 and 10 are a flowchart of general delivery of the double stent via the delivery device.
Figure 10:
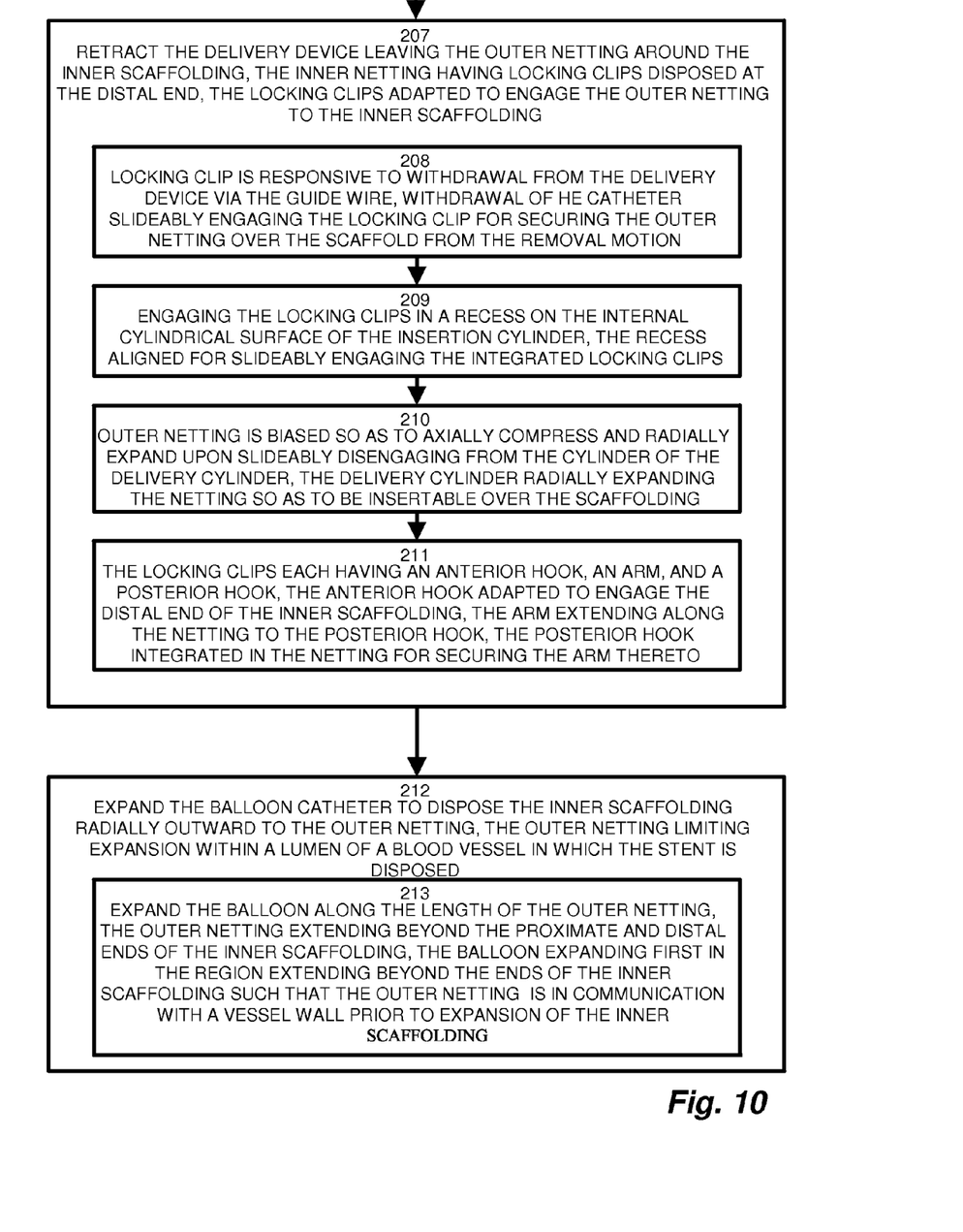

FIGS. 9 and 10 are a flowchart of general delivery of the particular configuration of the double stent via the delivery device 130 during an example delivery and installation of the stent 100. Referring to FIGS. 1, 9 and 10, the method for delivering the stent 100 device includes inserting a guide wire 134 to an afflicted area, such that the guide wire 134 is adapted for slideable insertion of a stent and catheter to an afflicted area, as depicted at step 200. The method involves delivering the inner scaffolding along the guide wire 134, such that the inner scaffolding 110 defines a cylindrical volume 115 around the catheter 104 having distal 142 and proximate 141 ridges and a balloon 116 catheter therebetween, in which the inner scaffolding 110 has flexible members 110' expandable radially and responsive to the balloon catheter 104, as shown at step 201.

The catheter 104 disposes, via a delivery device 130, an outer netting 120, in which the outer netting 120 defines a cylindrical shape having ends defining distal 124 and proximate 125 openings for disposing concentrically around the inner scaffolding 110, in which the outer netting 120 has a diameter larger than the diameter of the inner scaffolding 110, and the delivery device 130 has cylindrical body 131 and a limiting ridge 136 for engaging the outer netting 120 at the proximate opening 125 for slideable insertion around the inner scaffolding 110, such that the limiting ridge 136 is defined by an outer diameter larger than the outer netting 120 and an inner diameter smaller than the proximate restricting ridge 141 on the proximate end of the inner scaffolding 110, as depicted at step 202. In particular configurations, such as in FIG. 3, the stent 100 assembly further comprises a distal retainer 143 at the distal end of the inner scaffolding 110, such that the distal retainer 143 performs a similar function as the distal limiting ridge 142, as depicted at step 203.

The delivery device 130 advances the outer netting 120 over the inner scaffolding 110 from slideable movement of delivery device 130 along the guide wire 134 and catheter 104 to engage the limiting ridge 136 with the proximate ridge 141 of the inner scaffolding 120, as disclosed at step 204. The smaller inside diameter of the limiting ridge 136 stops forward advancement at a point where the outer netting 120 is substantially centered over the inner scaffolding 110. The outer netting 120 is slightly longer than the inner scaffolding 110, as depicted at step 205. The distal retainer 143 has a diameter larger then the unexpanded inner scaffolding 110, such that the distal retainer 143 is disposed such that a portion of the netting overlies the balloon 116 beyond the distal end 114 of the scaffolding 110, as shown at step 206. The overlying portion defines the extension region 102b; a symmetrical relation defines the extension region 102a on the proximate end.

The catheter 104 is employed in retracting the delivery device 130, thus leaving the outer netting 120 around the inner scaffolding 110. The inner netting 120 has locking clips disposed at the distal end 124, such that the locking clips 128 are adapted to engage the outer netting 120 to the inner scaffolding 110, as depicted at step 207. The locking clips 128 are responsive to withdrawal from the delivery device 130 via the guide wire 134 such that withdrawal of the catheter 104 slideably engages the locking clips 128 for securing the outer netting 120 over the scaffold 110 from the removal motion, as shown at step 208. In particular arrangements, removal engages the locking clips in a recess 129 on the internal cylindrical surface of the insertion cylinder 131, such that the recess is aligned for slideably engaging the integrated locking clips 128, as depicted at step 209. In alternate configurations, the distal retainer 143 is retracted through the inner scaffolding 110 as balloon expansion of the inner scaffolding 110 and outer netting 120 has radially expanded the stent 100 assembly. The outer netting 120 is biased so as to axially compress and radially expand upon slideably disengaging from the cylinder 131 of the delivery cylinder, such that the delivery cylinder radially compresses the netting 120 so as to be insertable between the scaffolding 110 and the lumen wall 106, as depicted at step 210.

In the example arrangement, the locking clips 128 each having an anterior hook 150, an arm 154, and a posterior hook 152, such that the anterior hooks 150 are adapted to engage the distal end 114 of the inner scaffolding 110, providing securement from the arm 154 extending along the netting 120 to the posterior hook 152, in which the posterior hook 152 is integrated in the netting 120 for securing the arm 154 thereto, disclosed at step 211.

Following forward advancement of the outer netting 120, installation includes expanding the balloon 116 catheter to dispose the inner scaffolding 110 radially outward to the outer netting 120, such that the outer netting 110 limits expansion within a lumen of a blood vessel in which the stent 100 is disposed, as discussed at step 212. The restricting ridges 141, 142 ensure that upon expanding the balloon 116 along the length of the outer netting 120, such that the outer netting 120 extends beyond the proximate 112 and distal 114 ends of the inner scaffolding 110, the balloon 116 expands first in the extension regions 102a, 102b extending beyond the ends 112, 114 of the inner scaffolding 110 such that the outer netting 120 is in communication with a vessel wall 106 prior to expansion of the inner scaffolding 110, as depicted at step 213. This preliminary expansion seals and secures the netting 120 and scaffolding 110 from emergence of the expansion bubbles 119 prior to the remainder of the stent 100, as discussed above.

Those skilled in the art should readily appreciate that the programs and methods for stent delivery and installation may be augmented by those skilled in the art without departing from the principles described above for advancing the double stent 100, withdrawing the delivery device 130 to secure the scaffolding 110 and netting 120 via locking clips 128, and selectively expanding first in the extension region define by the scaffolding 110 and netting. It will therefore be understood by those skilled in the art that various changes in form and details may be made therein without departing from the scope of the invention encompassed by the appended claims.

What is claimed is:

1. A method for delivering a stent device comprising:
   inserting a guide wire to an afflicted area, the guide wire adapted for slideable insertion of a stent and catheter to an afflicted area;
   delivering an inner scaffolding disposed on a balloon catheter along the guide wire, the inner scaffolding defining a cylindrical volume around a balloon of the balloon catheter disposed between distal and proximate ridges of the balloon catheter, the inner scaffolding having flexible members expandable radially and responsive to the balloon catheter;
   disposing, via a delivery device, an outer netting, the outer netting defining a cylindrical shape having ends defining distal and proximate openings for disposing concentrically around the inner scaffolding, the outer netting having a diameter larger than a diameter of the inner scaffolding, the delivery device having a cylindrical body and a limiting ridge for engaging the outer netting for slideable insertion around the inner scaffolding, the limiting ridge defined by an outer diameter larger than the outer netting and an inner diameter smaller than the proximate ridge on the balloon catheter;
   advancing the outer netting over the inner scaffolding from slideable movement of delivery device along the guide wire to engage the limiting ridge with the proximate ridge of the catheter on which the inner scaffolding is disposed at a point which the outer netting is substantially centered over the inner scaffolding; and
   retracting the delivery device leaving the outer netting disposed around the inner scaffolding, the outer netting having locking clips disposed at a distal end of the outer netting, the locking clips adapted to engage the outer netting to the inner scaffolding.

2. The method of claim 1 further comprising expanding the balloon catheter to dispose the inner scaffolding radially outward to the outer netting, the outer netting limiting expansion within a lumen of a blood vessel.

3. The method of claim 2 wherein the locking clips each having an anterior hook, an arm, and a posterior hook, the anterior hook adapted to engage a distal end of the inner scaffolding, the arm extending along the netting to the posterior hook, the posterior hook integrated in the netting for securing the arm thereto.

4. The method of claim 3 wherein the locking clips are responsive to withdrawal from the delivery device via the guide wire, withdrawal of the catheter slideably engaging the locking clips for securing the outer netting over the scaffold from the removal motion.

5. The method of claim 2 wherein outer netting is biased so as to axially compress and radially expand upon slideably disengaging from the cylindrical body of the delivery device, the delivery device radially compressing the netting so as to be insertable between the scaffolding and a lumen wall.

6. The method of claim 5 further comprising engaging the locking clips in a recess on the internal cylindrical surface of the-delivery device, the recess aligned for slideably engaging the integrated locking clips.

7. A delivery system for a multiple component vascular stent device comprising: a guide wire adapted for slideable insertion of a stent and catheter to an afflicted area; an inner scaffolding disposed on a balloon catheter adapted for slideable insertion along a guide wire, the inner scaffolding defining a cylindrical volume around a balloon of the balloon catheter disposed between distal and proximate ridges of the balloon catheter, the inner scaffolding having flexible members expandable radially and responsive to the balloon catheter; an outer netting disposed on a delivery device, the outer netting defining a cylindrical shape having ends defining distal and proximate openings for disposing concentrically around the inner scaffolding, the outer netting having a diameter larger than a diameter of the inner scaffolding, the delivery device having a cylindrical body and a limiting ridge for engaging the outer netting for slideable insertion around the inner scaffolding, the limiting ridge defined by an outer diameter larger than the outer netting and an inner diameter smaller than the proximate ridge on the inner scaffolding balloon catheter, wherein the delivery device is adapted to advance the outer netting over the inner scaffolding from slideable movement of the delivery device along the guide wire to engage the limiting ridge with the proximate ridge of the catheter on which the inner scaffolding is disposed at a point which the outer netting is substantially centered over the inner scaffolding, and wherein the outer netting comprises an integrated retention clip responsive to withdrawal from the delivery device via the guide wire to engage with the inner scaffolding.

8. The delivery system of claim 7 wherein the integrated retention clip has posterior hook integrated with the outer netting, an arm, and an anterior hook at a distal end of the arm, the anterior hook adapted to engage the distal end of the inner scaffolding upon withdrawal of the delivery device.

9. The delivery system of claim 8 wherein the inner scaffolding further comprises flexible members adapted to enlarge the cylindrical volume by radially expanding.

10. The delivery system of claim 9 wherein the balloon of the balloon catheter is coupled to an inflating channel adjacent the guide wire and responsive to an inflation tube for radial expansion within the inner scaffolding.

11. The delivery system of claim 7 wherein the delivery device has a cylindrical cavity adapted to concentrically contain the outer netting, the cylindrical cavity defined by a delivery tube adjacent to the limiting ridge, the delivery tube adapted to slideably engage the inner scaffolding to a limit of advancement defined by the limiting ridge engaging the inner scaffolding.

12. The delivery system of claim 7 further comprising restricting ridges at the proximate and distal ends of the inner scaffolding, the restricting ridges for defining and restricting advancement of the outer netting along the axis defined by the guide wire, the advancement limited such that the distal and proximate openings are adjacent to distal and proximate ends of the inner scaffolding.

13. The delivery system of claim 7 wherein withdrawal of the catheter slideably engages the integrated retention clip for securing the outer netting over the inner scaffolding from the removal motion.

14. The delivery system of claim 7 further comprising a recess on an internal cylindrical surface of the delivery device, the recess aligned for slideably engaging the integrated hooks.

* * * * *